US006590089B1

(12) United States Patent
Murry et al.

(10) Patent No.: US 6,590,089 B1
(45) Date of Patent: Jul. 8, 2003

(54) RVP-1 VARIANT DIFFERENTIALLY EXPRESSED IN CROHN'S DISEASE

(75) Inventors: Lynn E. Murry, Palo Alto, CA (US); Jennifer L. Hillman, Mountain View, CA (US); Y. Tom Tang, San Jose, CA (US); Chandra Patterson, Menlo Park, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/603,552

(22) Filed: Jun. 22, 2000

Related U.S. Application Data

(63) Continuation-in-part of application No. 09/106,920, filed on Jun. 29, 1998, now abandoned.

(51) Int. Cl.$^7$ .............................................. C07H 21/04
(52) U.S. Cl. .................. 536/23.5; 536/23.1; 536/24.31; 536/24.33; 435/69.1; 435/70.1; 435/320.1; 435/325
(58) Field of Search ............................ 536/23.5, 24.31, 536/24.33, 69.1, 23.1; 435/70.1, 320.1, 325, 69.1

(56) References Cited

PUBLICATIONS

Bowie, JU, et al. 1990, Deciphering the message in protein sequences: tolerance to amino acid substitutions, Science, vol. 247, pp. 306–1310.*

Burgess, WH, et al, 1990, Possible dissociation of the heparin–binding and mitogenic activities of heparin–binding (acidic fibroblast) growth factor–1, J Cell Biology, vol. 111, pages 2129–2138.*

Lazar, E, et al., 1988, Transforming growth factor alpha: mutation of aspartic acid 47 and leucine 48 results in different biological activities, Molecular and Cellular Biology, vol. 8, pp. 1247–1252.*

Briehl, M.M. and R.L. Miesfeld, "Isolation and Characterization of Transcripts Induced by Androgen Withdrawal and Apoptotic Cell Death in the Rat Ventral Prostate", Mol. Endocrinol., 5:1381–1388 (1991).

Katahira, J. et al., "*Clostridium perfringens* Enterotoxin Utilizes Two Structurally Related Membrane Proteins as Functional Receptors in Vivo", J. Biol. Chem., 272:26652–26658 (1997).

Morita, K. et al., "Claudin multigene family encoding four–transmembrane domain protein components of tight junction strands", Proc. Natl. Acad, Sci. USA, 96:511–516 (Jan. 1999).

Logsiger, C.S. et al., "Identification and Characterization of cDNA and the Structural Gene Encoding the Mouse Epithelial Membrane Protein–1", Genomics 36:379–387 (1996).

Ben–Porath, I. and Benvenisty, N., "Characterization of a tumor–associated gene, a member of a novel family of genes encoding membrane glycoproteins", Gene 183:69–75 (1996).

Katahira, J. et al., "Clostridium prfringens enterotoxin utilizes two structurally related Membrane proteins as functional receptors in vivo", GenBank Sequence Database (Accession BAA22986), National Center for Biotechnology Information, National Library of Medicine, Bethesda, Maryland, 20894 (GI 2570129).

Stanger, B.Z. et al., "RIP: A Novel Protein Containing a Death Domain That Interacts with Fas/APO–1 (CD95) in Yeast and Causes Cell Death", Cell 81:513–523 (May 19, 1995).

* cited by examiner

*Primary Examiner*—Anthony C. Caputa
*Assistant Examiner*—Stephen L. Rawlings
(74) *Attorney, Agent, or Firm*—Incyte Genomics, Inc.

(57) ABSTRACT

The invention provides a mammalian cDNA which encodes a mammalian an RVP-1 variant. It also provides for the use of the cDNA, fragments, complements, and variants thereof and of the encoded protein, portions thereof and antibodies thereto for diagnosis and treatment of Crohn's disease. The invention additionally provides expression vectors and host cells for the production of the protein and a transgenic model system.

9 Claims, 7 Drawing Sheets

FIGURE 1A

```
5'  GCC CGG GGC  AGC CCA GAG  GCT GGG AGG  GGG TGG ACT  TTT GGC CCG  TTT CGG
                9           18           27           36           45           54

TTA TTC CCT  CCA TCT CGT  CAA CAG CTG  CCG CGC GCA  GGC TTA GCT  CAT TCC TCT
               63           72           81           90           99          108

GAC CTG CCA  GGA AGC AGA  GAG ACC CAC  AGA GCA GGA  GGG AGG CAG  AAA GTG GAG
              117          126          135          144          153          162

ACG GAC CTG  AGC CCG AGG  AAG AGG CAG  GCA GAG GCT  GAT TCC ACC  CCA
              171          180          189          198          207          216

GCC TGC GAC  AAC CCT CCT  CCG CAG CAC  CTT CCA GTT  CCC TAG GGG  TTC
              225          234          243          252          261          270

TGC CCC TCT  CTG GGG CAC  CAG CAG CCC  AGG GTC CTG  CAT CCC ACC  ATG
     C   P   S    L   G   H    Q   Q   P    R   V   L    H   P   T    M
              279          288          297          306          315          324

TCG ATG GCT GTG GAA ACC TTT GGC TTC ATG AGG GTC CTG GGG CTG CTG ATG
     S   M   A   V   E   T   F   G   F   M   R   V   L   G   L   L   M
    333         342         351         360         369                378

CTG GGG GTG ACT CTG CCA AAC AGC TAC TGG CGA GCA ACT GTG TCC CAC GGG AAC
     L   G   V   T   L   P   N   S   Y   W   R   A   T   V   S   H   G   N
    387         396         405         414         423         432

GTC ATC ACC AAC ACC ATC TTC GAG AAC CTC TGG TTT AGC TGT GCC ACC GAC
     V   I   T   N   T   I   F   E   N   L   W   F   S   C   A   T   D
    441         450         459         468         477         486
```

```
TCC CTG GGC GTC TAC AAC TGC TGG GAG TTC CCG TCC ATG CTG GCC CTC TCT GGG
 S   L   G   V   Y   N   C   W   E   F   P   S   M   L   A   L   S   G
                495         504         513         522         531     540

TAT ATT CAG GCC TGC TGC CTA GGC CGG GCA CTC ATG ATC ACC GCC ATC CTC GGC TTC CTC
 Y   I   Q   A   C   R   L   G   A   L   M   I   T   A   I   L   G   F   L
                549         558         567         576         585     594

GGC CTC TTG CTA GGC ATA GCG GGG CTG CGC TGC CAC ATC CTC AAC ATT GGG GGC CTG GAG
 G   L   L   L   G   I   A   G   L   R   C   H   I   L   N   I   G   G   L   E
                603         612         621         630         639     648

CTC TCC AGG AAA GCT CAA GCT GGC GCC ATC CCC CAC CGC TGC CAC ATT CTG AAC GCC GCC CTC ATT CTG GCC
 L   S   R   K   A   Q   A   G   A   I   P   H   R   C   H   I   L   N   A   A   L   I   L   A
                657         666         675         684         693     702

GGT ATC TGG GGG ATG GTG CCC TCC TGG TAC AAG TAC GAG CTG GGC CCC GCC GCC CTC TGC CGG GAC
 G   I   W   G   M   V   P   S   W   Y   K   Y   E   L   G   P   A   A   L   C   R   D
                711         720         729         738         747     756

TTC TTC GAC CCC TTG TAC CCC GGA ACC AAG TAC GAG CTG GGC CCC GCC GCC CTC TAC
 F   F   D   P   L   Y   P   G   T   K   Y   E   L   G   P   A   A   L   Y
                765         774         783         792         801     810

CTG GGG TGG AGC GCC TCA CTG ATC TCC ATC CTG GGT GGC CTG GGC CTC TGC TCC
 L   G   W   S   A   S   L   I   S   I   L   G   G   L   G   L   C   S
                819         828         837         846         855     864
```

FIGURE 1B

```
         873         882         891         900         909         918
GCC TGC TGC GGC TCT GAC GAG CCA GCC AGC GCC CGG CCC TAC
 A   C   C   G   S   D   E   P   A   S   A   R   P   Y
         927         936         945         954         963         972
CAG GCT CCA GTG TCC GTG ATG CCC GTC GCC ACC TCG GAC CAA GAA GGC GAC AGC
 Q   A   P   V   S   V   M   P   V   A   T   S   D   Q   E   G   D   S
         981         990         999        1008        1017        1026
AGC TTT GGC AAA TAC GGC AGA AAC GCC TAC GTG TAG CAG CTC TGG CCC GTG GGC
 S   F   G   K   Y   G   R   N   A   Y   V   —   —   —   —   —   —   —
        1035        1044        1053        1062        1071        1080
CCG CTG TCT TCC CAC CCA AGG AGA GGG GAC TGG CCG GGG CCA TTC CCT ATA
        1089        1098        1107        1116        1125        1134
GTA ACT CAG GGG CGG CAC GCA CGG TCC GTA GCC CGC TCG GCA CGC CCC GTG TCT
        1143        1152        1161
TGA CCT CAT GGC CCT CAG GCT AGA CTG TCT T  3'
```

FIGURE 1C

```
  1  MS-MAVETFGFFMATVGLL--MLGVTLPNS   1456746
  1  MANAGLQLLGFILAFLGWIGAIVSTALPQ-   2057608
  1  MS-MGLEITGTALVLGWLGTIVCCALPM-    GI 2570129

28  YWRVSTVHGN-VITTNTIFENLWFSCATDS   1456746
 30  -WRIYSYAGDNIVTAQAMYEGLWMSCVSQS   2057608
 29  -WRVSAFIGSNIHTSQNIWEGLWMNCVVQS   GI 2570129

57  LGVYNCWEFPSMLALSGYIQACRALMITAI   1456746
 59  TGQIQCKVFDSLLNLSSTLQATRALMVVGI   2057608
 58  TGQMQCKVYDSLLALPQDLQAARALIVVAI   GI 2570129

87  LLGFLGLLLGIAGLRCTNHGGLELSRKAQA   1456746
 89  LLGVIAIFVATVGMKCMKCLEDDEVQKMRM   2057608
 88  LLAAFGLLVALVGAQCTNCVQDDTA-KAKI   GI 2570129

117  GGHRRALHILAGICGMVAISWYAFNITRDF   1456746
119  AVIGGAIFLLAGLAILVATAWYGNRIVQEF   2057608
117  TIVAGVLFLLAALLTLVPVSWSANTHIRDF   GI 2570129
```

The Electronic Northern based on Project ID: 1456746

| Library | Library Description* | Abun | Pct Abun |
|---|---|---|---|
| SINTBST01 | sm intestine, ileum, Crohn's, 18F | 4 | 0.0673 |
| SINTNOT18 | sm intestine, aw/carcinoid, 59M | 2 | 0.0599 |
| COLNNOT19 | colon, cecum, aw/Crohn's, 18F | 2 | 0.0585 |
| LUNGNOT04 | lung, 2M | 3 | 0.0549 |
| SININOT05 | sm intestine, ileum, aw/carcinoid, 30F | 2 | 0.0523 |
| OVARNOT12 | ovary, aw/leiomyomata, 36F | 2 | 0.0491 |
| SINTNOT02 | sm intestine, 55F | 1 | 0.0346 |
| OVARNOT07 | ovary, aw/follicular cysts, 28F | 1 | 0.0269 |
| ESOGNOT03 | esophagus, aw/adenoCA, 53M | 1 | 0.0263 |
| PTHYNOT04 | parathyroid, aw/parathyroid CA, 44M | 1 | 0.0257 |
| SININOT04 | sm intestine, ileum, Crohn's, 26M | 1 | 0.0241 |
| KIDNNOT32 | kidney, 49M | 1 | 0.0177 |
| TLYMNOT03 | lymphocytes, nonactivated Th1 cells | 1 | 0.0168 |
| BRSTTUT15 | breast tumor, adenoCA, 46F, m/BRSTNOT17 | 1 | 0.0152 |
| COLNFET02 | colon, fetal, 20wF | 1 | 0.0143 |
| KIDNNOT19 | kidney, aw/renal cell CA, 65M, m/KIDNTUT15 | 1 | 0.0143 |
| UTRSTUT05 | uterine tumor, leiomyoma, 41F, m/UTRSNOT12, UTRSNON03 | 1 | 0.0130 |
| TESTNOT11 | testis, 16M | 1 | 0.0118 |
| DRGTNON04 | ganglion, dorsal root, thoracic, aw/lymphoma, 32M, NORM | 1 | 0.0113 |
| BRSTTUT03 | breast tumor, lobular CA, 58F, m/BRSTNOT05 | 1 | 0.0099 |
| BRSTNOT04 | breast, aw/ductal CA, 62F | 1 | 0.0096 |
| PANCTUT02 | pancreatic tumor, anaplastic CA, 45F | 1 | 0.0086 |

FIGURE 3A

Not found in:

| Library | Clone Count | Library Description* |
|---|---|---|
| COLADIT05 | 2587 | colon, ascending, CUC, 32M |
| COLANOT02 | 3979 | colon, ascending, CUC, 25F |
| COLAUCT01 | 4034 | colon, ascending, CUC, 74M |
| COLNNOT13 | 3217 | colon, ascending, mw/CUC, 28M |
| COLNNOT23 | 3787 | colon, ulcerative colitis, 16 |
| COLNUCT03 | 3676 | colon, CUC, 69M |
| COLSUCT01 | 2429 | colon, sigmoid, CUC, 70M |
| SINIUCT01 | 3307 | sm intestine, ileum, mw/CUC, 42M |
| SINTNOT13 | 3642 | sm intestine, ileum, mw/CUC, 25F |

\* None of the libraries shown above were biased toward rare clones using normalization protocols; i.e, abundant clones were not subtracted during library construction.

FIGURE 3B

```
                            SEQUENCE LISTING

<160> NUMBER OF SEQ ID NOS:    13

<210> SEQ ID NO 1
<211> LENGTH: 228
<212> TYPE: PRT
<213> ORGANISM: Homo sapiens
<220> FEATURE:
<221> NAME/KEY: misc_feature
<223> OTHER INFORMATION: Incyte ID No: 1456746CD1

<400> SEQUENCE: 1

Met Ser Met Ala Val Glu Thr Phe Gly Phe Phe Met Ala Thr Val
  1               5                  10                  15

Gly Leu Leu Met Leu Gly Val Thr Leu Pro Asn Ser Tyr Trp Arg
                 20                  25                  30

Val Ser Thr Val His Gly Asn Val Ile Thr Thr Asn Thr Ile Phe
                 35                  40                  45

Glu Asn Leu Trp Phe Ser Cys Ala Thr Asp Ser Leu Gly Val Tyr
                 50                  55                  60

Asn Cys Trp Glu Phe Pro Ser Met Leu Ala Leu Ser Gly Tyr Ile
                 65                  70                  75

Gln Ala Cys Arg Ala Leu Met Ile Thr Ala Ile Leu Leu Gly Phe
                 80                  85                  90

Leu Gly Leu Leu Leu Gly Ile Ala Gly Leu Arg Cys Thr Asn Ile
                 95                 100                 105

Gly Gly Leu Glu Leu Ser Arg Lys Ala Gln Ala Gly Gly His Arg
                110                 115                 120

Arg Ala Leu His Ile Leu Ala Gly Ile Cys Gly Met Val Ala Ile
                125                 130                 135

Ser Trp Tyr Ala Phe Asn Ile Thr Arg Asp Phe Phe Asp Pro Leu
                140                 145                 150

Tyr Pro Gly Thr Lys Tyr Glu Leu Gly Pro Ala Leu Tyr Leu Gly
                155                 160                 165

Trp Ser Ala Ser Leu Ile Ser Ile Leu Gly Gly Leu Cys Leu Cys
                170                 175                 180

Ser Ala Cys Cys Cys Gly Ser Asp Glu Asp Pro Ala Ala Ser Ala
                185                 190                 195

Arg Arg Pro Tyr Gln Ala Pro Val Ser Val Met Pro Val Ala Thr
                200                 205                 210

Ser Asp Gln Glu Gly Asp Ser Ser Phe Gly Lys Tyr Gly Arg Asn
                215                 220                 225

Ala Tyr Val

<210> SEQ ID NO 2
<211> LENGTH: 1165
<212> TYPE: DNA
<213> ORGANISM: Homo sapiens
<220> FEATURE:
<221> NAME/KEY: misc_feature
<223> OTHER INFORMATION: Incyte ID No: 1456746CB1
```

<400> SEQUENCE: 2

```
gcccggggca gcccagaggc tgggggagg gggtggactt ttggcccgtt tcggttattc      60
cctccatctc gtcaacagct gccgcgcgca ggcttagctc attcctctga cctgccagga    120
agcagagaga cccacagagc aggagggagg cagaaagtgg agacggacct gagcccgagg    180
aagaggcagg cagaggctga ggctgattcc accccagcct gcctggacaa ccctccttag    240
ccgcagcccc ttccagttcc ctaggggttc tgcccctccc cctctctggg gcaccagccc    300
cccagggtcc tgcatcccac catgtcgatg gctgtggaaa cctttggctt cttcatggca    360
actgtggggc tgctgatgct gggggtgact ctgccaaaca gctactggcg agtgtccact    420
gtgcacggga acgtcatcac caccaacacc atcttcgaga acctctggtt tagctgtgcc    480
accgactccc tgggcgtcta caactgctgg gagttcccgt ccatgctggc cctctctggg    540
tatattcagg cctgccgggc actcatgatc accgccatcc tcctgggctt cctcggcctc    600
ttgctaggca tagcgggcct gcgctgcacc aacattgggg gcctggagct ctccaggaaa    660
gctcaagctg gcgccaccg cagggccctc cacattctgg ccggtatctg cgggatggtg    720
gccatctcct ggtacgcctt caacatcacc cgggacttct tcgacccctt gtaccccgga    780
accaagtacg agctgggccc cgccctctac ctggggtgga gcgcctcact gatctccatc    840
ctgggtggcc tctgcctctg ctccgcctgc tgctgcggct ctgacgagga cccagccgcc    900
agcgcccggc ggccctacca ggctccagtg tccgtgatgc ccgtcgccac ctcggaccaa    960
gaaggcgaca gcagctttgg caaatacggc agaaacgcct acgtgtagca gctctggccc   1020
gtgggcccgc tgtcttccca ctgcccaagg agaggggact ggccggggcc attccctata   1080
gtaactcagg ggcggcacgc acggtccgta gcccgctcgg cacgccccgt gtcttgacct   1140
catggccctc aggctagact gtctt                                         1165
```

<210> SEQ ID NO 3
<211> LENGTH: 237
<212> TYPE: DNA
<213> ORGANISM: Homo sapiens
<220> FEATURE:
<221> NAME/KEY: misc_feature
<223> OTHER INFORMATION: Incyte ID No: 1456746H1
<221> NAME/KEY: unsure
<222> LOCATION: 124-125, 131
<223> OTHER INFORMATION: a, t, c, g, or other

<400> SEQUENCE: 3

```
gcagcccaga ggctgggggg aggggtgga cttttggccc gtttcggtta ttccctccat      60
ctcgtcaaca gctgccgcgc gcaggcttag ctcattcctc tgacctgcca ggaagcagag    120
agannccaca ngagcaggag ggaggcagaa agtggagacg gacctgagcc cgaggaagag    180
gcaggcagag gctgaggctg attccacccc agcctgcctg acaaccctc cttagcc       237
```

<210> SEQ ID NO 4
<211> LENGTH: 183
<212> TYPE: DNA
<213> ORGANISM: Homo sapiens
<220> FEATURE:
<221> NAME/KEY: misc_feature
<223> OTHER INFORMATION: Incyte ID No: 1512130H1

<400> SEQUENCE: 4

```
ggggctgttg ggctggctcc gtcgcagagg ggagatggga aaggctgaca actgtgccca      60
cccccagggt atattcaggc ctgccgggca ctcatgatca ccgccatcct cctgggcttc    120
```

```
ctcggcctct tgctaggcat agcgggcctg cgctgcacca acattgggg cctggagctc      180 tcc                                                                   183

<210> SEQ ID NO 5
<211> LENGTH: 524
<212> TYPE: DNA
<213> ORGANISM: Homo sapiens
<220> FEATURE:
<221> NAME/KEY: misc_feature
<223> OTHER INFORMATION: Incyte ID No: 1456746T6
<221> NAME/KEY: unsure
<222> LOCATION: 192, 328, 397, 420, 496, 503, 506
<223> OTHER INFORMATION: a, t, c, g, or other

<400> SEQUENCE: 5
tggtatggca ctgtggacgt gcactgtgtg tgtgcgccat agcgtgcacc ctaactctgc      60
tccccagcta ggatgtaagc tcccggaggc agccgctcac tcttatcttc gaagtccctc     120
ccacacctgg ccgtggccag cccctactgg gagctcaaga acactgccg atgggctgat     180 ttgcagccag gngatctggg gagtacagat gaggcagggg tgagcaggtg tccatgcagc     240
agggtagggg aggtgagcat gaggagtggg aattggagag gagattagat gaggacaaag     300
cagcctgaag tctgcggttg aggggganncc ccgccccatc accttccccc agttaccggc    360
cagaatgtgg aggggccctg cggttgccgc caacttnggt ttcctggaga actccagggn     420
cccaaatgtt ggtgcagcga aggccccgct atgcctaagc aagagggccg aaggaagcca     480
agaagattgc ggtganttat tanttnnccg gaaggcctta attt                      524

<210> SEQ ID NO 6
<211> LENGTH: 253
<212> TYPE: DNA
<213> ORGANISM: Homo sapiens
<220> FEATURE:
<221> NAME/KEY: misc_feature
<223> OTHER INFORMATION: Incyte ID No: 2922036H1

<400> SEQUENCE: 6
tgggcttcct cggcctcttg ctaggcatag cgggcctgcg ctgcaccaac attggggggcc    60 tggagctctc caggaaagcc aagctggcgg ccaccgcagg gccctccaca ttctggccgg    120
tatctgcggg atggtggcca tctcctggta cgccttcaac atcacccggg acttcttcga    180 cccttgtac cccggaacca agtacgagct gggccccgcc tctacctggg ggtggagcgc     240
ctcactgatc tcc                                                       253

<210> SEQ ID NO 7
<211> LENGTH: 541
<212> TYPE: DNA
<213> ORGANISM: Homo sapiens
<220> FEATURE:
<221> NAME/KEY: misc_feature
<223> OTHER INFORMATION: Incyte ID No: 1430349F1
<221> NAME/KEY: unsure
<222> LOCATION: 350, 473, 480, 531
<223> OTHER INFORMATION: a, t, c, g, or other

<400> SEQUENCE: 7
gcgctgcacc aacattgggg gcctggagct ctccaggaaa gccaagctgg cggccaccgc     60
agggccctcc acattctggc cggtatctgc gggatggtgg ccatctcctg gtacgccttc    120
aacatcaccc gggacttctt cgaccccttg taccccggaa ccaagtacga gctgggcccc    180
gccctctacc tgggggtgga gcgcctcact gatctccatc ctggtggcct ctgcctctgc    240
```

```
tccgcctgct gctgcggctc tgacgaggac ccagccgcca gcgcccggcg gccctaccag      300
gctccagtgt ccgtgatgcc cgtcgccacc tcggaccaag aaggcgacan agctttggca      360
aatacggcag aaacgcctac cgtgtagcagt ctggcccgtg ggcccgctgt ttccactgcc     420
caaaggagag ggacttggcc gggccattcc ctatagtaac tcaagggcgg cangcccggn      480
tccgtagccc cgcccggcag ggcccgtgtt tgaatccatg gcctcaaggc naaaaatgtc      540
t                                                                     541

<210> SEQ ID NO 8
<211> LENGTH: 427
<212> TYPE: DNA
<213> ORGANISM: Rattus norvegicus
<220> FEATURE:
<221> NAME/KEY: misc_feature
<223> OTHER INFORMATION: Incyte ID No: 702156327H1

<400> SEQUENCE: 8
ctgggagtct ccaactgctg ggacttcccg tccatgctgg ccctctctgg ctatgtccag       60
ggctgccgag ctctcatgat caccgccatc ctcctgggct tccttgggcc tctttctagg     120
catggtgggg ctccgctgca ccaacgtggg caacatcgac ctctccagga aggccaagct     180
gctggccatt gcagggggcct tccacatact tgctggagcc tgtggcatgg ttgctatctc    240
atggtacgct gtcaacatca ccaccgactt cttcaacccc ctgtatgctg gaaccaagta    300
tgaactgggc tctgccctct acttgggctg gagcgcctct ctgctctcca tcctgggcgg   360
catctgtgtc ttctccacct gctgctgtga ctccaaggag gacccagcca ccagggtggg  420
acttccc                                                             427

<210> SEQ ID NO 9
<211> LENGTH: 279
<212> TYPE: DNA
<213> ORGANISM: Rattus norvegicus
<220> FEATURE:
<221> NAME/KEY: misc_feature
<223> OTHER INFORMATION: Incyte ID No: 700276486H1

<400> SEQUENCE: 9
cctgacctcc agaagacagc agacaagaac cgcagctgga tgagcttccc ttcaaccttc      60
tccctcctca gtcttcctta gcatctcacc tggaggagcc acctctatcc caatccctgg    120
ggctcaagcc cccttgcggg acctgcatcc cagcatgtcg atagctgtgg agacctttgg    180
tttcttcatg tcagccctgg gactgctgat gctggggtg accttccaa acagctactg     240 gagagtgtct accgtccatg ggaacgtcat caccactaa                            279

<210> SEQ ID NO 10
<211> LENGTH: 208
<212> TYPE: DNA
<213> ORGANISM: Rattus norvegicus
<220> FEATURE:
<221> NAME/KEY: misc_feature
<223> OTHER INFORMATION: Incyte ID No: 700277065H1

<400> SEQUENCE: 10
actggccatt gcagggggcct tccacatact tgctggagcc tgtggcatgg ttgctatctc      60
atggtacgct gtcaacatca ccaccgactt cttcaacccc ctgtatgctg gaaccaagta    120
tgaactgggc tctgccctct acttgggctg gagcgcctct ctgctctcca tcctgggcgg    180
catctgtgtc ttctcacctg ctgctgtg                                        208
```

<210> SEQ ID NO 11
<211> LENGTH: 323
<212> TYPE: DNA
<213> ORGANISM: Rattus norvegicus
<220> FEATURE:
<221> NAME/KEY: misc_feature
<223> OTHER INFORMATION: Incyte ID No: 218929_Rn.1 g4325319 Mouse
      claudin-15 mRNA, partial  4e-45

<400> SEQUENCE: 11
gccaggaagc agagcctccc agagaccggg cagaagcaat cagacctgac ctccagaaga      60
cagcagacaa gaaccgcagc tggatgagct tcccttcaac cttctccctc ctcagtcttc     120
cttagcatct cacctggagg agccacctct atcccaatcc ctggggctca agcccccttg     180
cgggacctgc atcccagcat gtcgatagct gtggagacct ttggtttctt catgtcagcc     240 ctggactgc tgatgctggg ggtgacccctt ccaaacagct actggagagt gtctaccgtc     300
catgggaacg tcatcaccac taa                                             323

<210> SEQ ID NO 12
<211> LENGTH: 211
<212> TYPE: PRT
<213> ORGANISM: Homo sapiens
<220> FEATURE:
<221> NAME/KEY: misc_feature
<223> OTHER INFORMATION: Incyte ID No: 2057608CD1

<400> SEQUENCE: 12

Met Ala Asn Ala Gly Leu Gln Leu Leu Gly Phe Ile Leu Ala Phe
 1               5                  10                  15

Leu Gly Trp Ile Gly Ala Ile Val Ser Thr Ala Leu Pro Gln Trp
                20                  25                  30

Arg Ile Tyr Ser Tyr Ala Gly Asp Asn Ile Val Thr Ala Gln Ala
                35                  40                  45

Met Tyr Glu Gly Leu Trp Met Ser Cys Val Ser Gln Ser Thr Gly
            50                  55                  60

Gln Ile Gln Cys Lys Val Phe Asp Ser Leu Leu Asn Leu Ser Ser
            65                  70                  75

Thr Leu Gln Ala Thr Arg Ala Leu Met Val Val Gly Ile Leu Leu
            80                  85                  90

Gly Val Ile Ala Ile Phe Val Ala Thr Val Gly Met Lys Cys Met
            95                 100                 105

Lys Cys Leu Glu Asp Asp Glu Val Gln Lys Met Arg Met Ala Val
               110                 115                 120

Ile Gly Gly Ala Ile Phe Leu Leu Ala Gly Leu Ala Ile Leu Val
               125                 130                 135

Ala Thr Ala Trp Tyr Gly Asn Arg Ile Val Gln Glu Phe Tyr Asp
               140                 145                 150

Pro Met Thr Pro Val Asn Ala Arg Tyr Glu Phe Gly Gln Ala Leu
               155                 160                 165

Phe Thr Gly Trp Ala Ala Ala Ser Leu Cys Leu Leu Gly Gly Ala
               170                 175                 180

Leu Leu Cys Cys Ser Cys Pro Arg Lys Thr Thr Ser Tyr Pro Thr
               185                 190                 195

Pro Arg Pro Tyr Pro Lys Pro Ala Pro Ser Ser Gly Lys Asp Tyr
               200                 205                 210

Val

<210> SEQ ID NO 13
<211> LENGTH: 220
<212> TYPE: PRT
<213> ORGANISM: Homo sapiens
<220> FEATURE:
<221> NAME/KEY: misc_feature
<223> OTHER INFORMATION: GenBank No: g2570129

<400> SEQUENCE: 13

```
Met Ser Met Gly Leu Glu Ile Thr Gly Thr Ala Leu Ala Val Leu
 1               5                  10                  15

Gly Trp Leu Gly Thr Ile Val Cys Cys Ala Leu Pro Met Trp Arg
                20                  25                  30

Val Ser Ala Phe Ile Gly Ser Asn Ile Ile Thr Ser Gln Asn Ile
                35                  40                  45

Trp Glu Gly Leu Trp Met Asn Cys Val Val Gln Ser Thr Gly Gln
                50                  55                  60

Met Gln Cys Lys Val Tyr Asp Ser Leu Leu Ala Leu Pro Gln Asp
                65                  70                  75

Leu Gln Ala Ala Arg Ala Leu Ile Val Val Ala Ile Leu Leu Ala
                80                  85                  90

Ala Phe Gly Leu Leu Val Ala Leu Val Gly Ala Gln Cys Thr Asn
                95                  100                 105

Cys Val Gln Asp Asp Thr Ala Lys Ala Lys Ile Thr Ile Val Ala
                110                 115                 120

Gly Val Leu Phe Leu Leu Ala Ala Leu Leu Thr Leu Val Pro Val
                125                 130                 135

Ser Trp Ser Ala Asn Thr Ile Ile Arg Asp Phe Tyr Asn Pro Val
                140                 145                 150

Val Pro Glu Ala Gln Lys Arg Glu Met Gly Ala Gly Leu Tyr Val
                155                 160                 165

Gly Trp Ala Ala Ala Leu Gln Leu Leu Gly Gly Ala Leu Leu
                170                 175                 180

Cys Cys Ser Cys Pro Pro Arg Glu Lys Lys Tyr Thr Ala Thr Lys
                185                 190                 195

Val Val Tyr Ser Ala Pro Arg Ser Thr Gly Pro Gly Ala Ser Leu
                200                 205                 210

Gly Thr Gly Tyr Asp Arg Lys Asp Tyr Val
```

RVP-1 VARIANT DIFFERENTIALLY EXPRESSED IN CROHN'S DISEASE

The application is a continuation-in-part of U.S. Ser. No. 09/106,920 filed Jun. 29, 1998 now abandoned.

FIELD OF THE INVENTION

This invention relates to a mammalian cDNA which encodes an RVP-1 variant and to the use of the cDNA and the encoded protein in the diagnosis and treatment of cell proliferative disorders, particularly cancers, and autoimmune disorders, particularly Crohn's disease.

BACKGROUND OF THE INVENTION

Phylogenetic relationships among organisms have been demonstrated many times, and studies from a diversity of prokaryotic and eukaryotic organisms suggest a more or less gradual evolution of molecules, biochemical and physiological mechanisms, and metabolic pathways. Despite different evolutionary pressures, the proteins of nematode, fly, rat, and man have common chemical and structural features and generally perform the same cellular function. Comparisons of the nucleic acid and protein sequences from organisms where structure and/or function are known accelerate the investigation of human sequences and allow the development of model systems for testing diagnostic and therapeutic agents for human conditions, diseases, and disorders.

Apoptosis is the genetically controlled process by which unneeded or defective cells undergo programmed cell death. Apoptotic events are part of the normal developmental programs of many multicellular organisms. Selective elimination of cells is as important for morphogenesis and tissue remodeling as is cell proliferation and differentiation. Apoptosis is a critical component of the immune response. Cytotoxic T-cells and natural killer cells are active in systemic defense through induction of apoptosis in tumor cells and virus-infected cells. In addition, immune cells that fail to distinguish self molecules from foreign molecules must be eliminated by apoptosis to avoid an autoimmune response.

Apoptotic cells undergo distinct morphological changes including shrinkage, nuclear and cytoplasmic condensation, and alterations in plasma membrane topology. Biochemically, apoptotic cells are characterized by increased intracellular calcium concentration, fragmentation of chromosomal DNA into nucleosomal-length units, and expression of novel cell surface components. The molecular mechanisms of apoptosis are highly conserved, and many of the key protein regulators and effectors are known. Apoptosis generally proceeds in response to a signal which is transduced intracellularly and results in altered patterns of gene expression and protein activity. Signaling molecules such as hormones and cytokines are known to regulate apoptosis both positively and negatively through their interactions with cell surface receptors. Transcription factors also play an important role in the onset of apoptosis. A number of downstream effector molecules, especially proteases, have been implicated in the process.

The rat ventral prostate is a model system for the study of hormone-regulated apoptosis. Messenger RNA transcripts including those encoding the rat protein, RVP-1, are upregulated when epithelial cells undergo apoptosis in response to androgen deprivation (Briehl and Miesfeld (1991) Mol Endocrinol 5:1381–1388). The human homolog, hRVP1, is 89% identical to the rat protein, 220 amino acids in length, and contains four transmembrane domains (Katahira et al (1997) J Biol Chem 272:26652–26658). hRVP1, also known as claudin 3 (g2459928), is highly expressed in the lung, intestine, and liver and functions as a low affinity receptor for the *Clostridium perfringens* enterotoxin, a causative agent of diarrhea in humans and other animals.

Claudins are a multi-gene family of four transmembrane proteins (Morita et al (1999) Proc Natl Acad Sci 96:511–516) which have been found to form tight junctions (TJs). For example, claudin 1 is a protein of 220 residues that incorporates into TJ strands. TJs form a belt-like network of strands within plasma membranes at the most apical region of polarized epithelial and endothelial cells. This network creates a permeability barrier to the lateral diffusion of lipids and proteins between apical and basolateral membrane domains and maintains cellular polarity. In the region between adjacent cells where two opposing membranes come together, tight junction strands from each cell associate to form a paired strand. These paired strands create permeability barriers for the diffusion of solutes through the paracellular pathway. Claudins belong to a superfamily of epithelial membrane proteins (EMPs) known to carry out functions in cell growth, differentiation, and apoptosis (Lobsiger et al (1996) Genomics 36:379–387). Aberrant expression of EMPs has been associated with tumorigenesis (Ben-Porath and Benvenisty (1996) Gene 183:69–75).

Many gastrointestinal disorders, including peptic ulcers, gastritis, ulcerative colitis and Crohn's disease, are characterized by the same symptoms. These symptoms include severe abdominal pain, cramps, fever, diarrhea, anemia, and weight loss. After establishing that the symptoms are not due to a infectious agent, it becomes necessary to diagnose them in order to provide appropriate treatment. Crohn's disease which is an autoimmune disorder appears to enter an acute phase in response to stress and the ulcerous lesions are particularly active in forming adhesions that must be removed surgically. At the present time, there are no specific therapies for this disorder.

The discovery of a mammalian cDNA encoding an RVP-1 variant and the polynucleotides encoding it satisfies a need in the art by providing new compositions which are useful in the diagnosis and treatment of cell proliferative disorders, particularly cancers, and autoimmune disorders, particularly Crohn's disease.

SUMMARY OF THE INVENTION

The invention is based on the discovery of a mammalian cDNA which encodes a mammalian RVP-1 variant (MAPOP-1) which is useful in the diagnosis and treatment of cell proliferative disorders, particularly cancers, and autoimmune disorders, particularly Crohn's disease.

The invention provides an isolated mammalian cDNA or a fragment thereof encoding a mammalian protein or a portion thereof selected from the group consisting of an amino acid sequence of SEQ ID NO:1, a variant having 85% identity to the amino acid sequence of SEQ ID NO: 1, an antigenic epitope of SEQ ID NO:1, an oligopeptide of SEQ ID NO:1, and a biologically active portion of SEQ ID NO:1. The invention also provides an isolated mammalian cDNA or the complement thereof selected from the group consisting of a nucleic acid sequence of SEQ ID NO:2, a fragment selected from SEQ ID NOs:3–7, a variant selected from SEQ ID NOs:8–11 and having at least 80% identity to the nucleic acid sequence of SEQ ID NO:2, or an oligonucleotide of SEQ ID NO:2. The invention additionally provides a composition, a substrate, and a probe comprising the cDNA, or the complement of the cDNA, encoding the protein having the amino acid sequence of SEQ ID NO:1. The invention further provides a vector containing the cDNA, a host cell containing the vector, and a method for using the cDNA to produce MAPOP-1 comprising culturing the host cell under conditions for protein expression and recovering the protein from cell culture. The invention still further provides a transgenic cell line or organism comprising the vector containing the cDNA encoding an MAPOP-1. The invention additionally provides a mammalian fragment, or the complement thereof, selected from the group consisting of SEQ ID NOs:8–11. In one aspect, the invention provides a substrate containing at least one of these fragments. In a second aspect, the invention provides a probe comprising the fragment which can be used in methods of detection, screening, and purification. In a further aspect, the probe is a single stranded complementary RNA or DNA molecule.

The invention provides a method for using a cDNA to detect the differential expression of a nucleic acid in a sample comprising hybridizing a probe to the nucleic acids, thereby forming hybridization complexes and comparing hybridization complex formation with a standard, wherein the comparison indicates the differential expression of the cDNA in the sample. In one aspect, the method of detection further comprises amplifying the nucleic acids of the sample prior to hybridization. In another aspect, the method showing differential expression of the cDNA is used to diagnose a cell proliferative disorder, particularly cancer, or an autoimmune disorder, particularly Crohn's disease. In another aspect, the cDNA or a fragment or a complement thereof may comprise an element on an array.

The invention additionally provides a method for using a cDNA or a fragment or a complement thereof to screen a library or plurality of molecules or compounds to identify at least one ligand which specifically binds the cDNA, the method comprising combining the cDNA with the molecules or compounds under conditions allowing specific binding, and detecting specific binding to the cDNA, thereby identifying a ligand which specifically binds the cDNA. In one aspect, the molecules or compounds are selected from aptamers, DNA molecules, RNA molecules, peptide nucleic acids, artificial chromosome constructions, peptides, transcription factors, repressors, and regulatory molecules.

The invention provides a purified mammalian protein or a portion thereof selected from the group consisting of an amino acid sequence of SEQ ID NO:1, a variant having 85% identity to the amino acid sequence of SEQ ID NO:1, an antigenic epitope of SEQ ID NO:1, an oligopeptide of SEQ ID NO:1, and a biologically active portion of SEQ ID NO:1. The invention also provides a composition comprising the purified protein or a portion thereof in conjunction with a pharmaceutical carrier. The invention further provides a method of using the MAPOP-1 to treat a subject with Crohn's disease comprising administering to a patient in need of such treatment the composition containing the purified protein. The invention still further provides a method for using a protein to screen a library or a plurality of molecules or compounds to identify at least one ligand, the method comprising combining the protein with the molecules or compounds under conditions to allow specific binding and detecting specific binding, thereby identifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with Crohn's disease.

The invention provides a method of using a mammalian protein to screen a subject sample for antibodies which specifically bind the protein comprising isolating antibodies from the subject sample, contacting the isolated antibodies with the protein under conditions that allow specific binding, dissociating the antibody from the bound-protein, and comparing the quantity of antibody with known standards, wherein the presence or quantity of antibody is diagnostic of Crohn's disease.

The invention also provides a method of using a mammalian protein to prepare and purify antibodies comprising immunizing a animal with the protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified antibodies.

The invention provides a purified antibody which binds specifically to MAPOP-1. The invention also provides a method of using an antibody to diagnose Crohn's disease comprising combining the antibody with a sample under conditions to allow specific binding, detecting the antibody complex, and comparing the quantity of antibody complex to known standards, thereby establishing the presence of Crohn's disease. The invention further provides a method of using an antibody to treat Crohn's disease comprising administering to a patient in need of such treatment a pharmaceutical composition comprising the purified antibody.

The invention provides a method for inserting a marker gene into the genomic DNA of a mammal to disrupt the expression of the endogenous polynucleotide. The invention also provides a method for using a cDNA to produce a mammalian model system, the method comprising constructing a vector containing the cDNA selected from SEQ ID NOs:3–11, transforming the vector into an embryonic stem cell, selecting a transformed embryonic stem, microinjecting the transformed embryonic stem cell into a mammalian blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, mammalian model system.

BRIEF DESCRIPTION OF THE FIGURES

FIGS. 1A, 1B, and 1C show the RVP-1 variant, MAPOP-1 (SEQ ID NO:1), encoded by the cDNA (SEQ ID NO:2). The alignment was produced using MACDNASIS PRO software (Hitachi Software Engineering, South San Francisco, Calif.).

FIGS. 2A and 2B show the amino acid sequence alignments between MAPOP-1 (1456746; SEQ ID NO:1), 2057608 (claudin 1; SEQ ID NO:12) and human hRVP1 (g2570129 (claudin 3); SEQ ID NO:13). The alignments were produced using the MEGALIGN program (DNASTAR, Madison, Wis.).

FIGS. 3A and 3B shows the northern analysis for MAPOP-1 produced using the LIFESEQ Gold database (Incite Genomics, Palo Alto, Calif.). FIG. 3A shows the differential expression of SEQ ID NO:2 in Crohn's disease, the first column presents the tissue categories, the second column, the number of clones in the tissue category, the third column, the number of libraries in which at least one transcript was found, the fourth column, absolute abundance of the transcript, and the fifth column, percent abundance of the trancript. FIG. 3B shows the ulcerative colitis libraries in which SEQ ID NO:2 was never expressed, the first column lists the library name, the second column, the number of clones sequenced for that library, and the third column, description of the tissue.

DESCRIPTION OF THE INVENTION

It is understood that this invention is not limited to the particular machines, materials and methods described. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"MAPOP-1" refers to a purified protein obtained from any mammalian species, including bovine, canine, murine, ovine, porcine, rodent, simian, and preferably the human species, and from any source, whether natural, synthetic, semi-synthetic, or recombinant.

"Array" refers to an ordered arrangement of at least two cDNAs on a substrate. At least one of the cDNAs represents a control or standard sequence, and the other, a cDNA of diagnostic interest. The arrangement of from about two to about 40,000 cDNAs on the substrate assures that the size and signal intensity of each labeled hybridization complex formed between a cDNA and a sample nucleic acid is individually distinguishable.

The "complement" of a cDNA of the Sequence Listing refers to a nucleic acid molecule which is completely complementary over its full length and which will hybridize to the cDNA or an mRNA under conditions of high stringency.

"cDNA" refers to an isolated polynucleotide, nucleic acid molecule, or any fragment or complement thereof. It may have originated recombinantly or synthetically, be double-stranded or single-stranded, represent coding and/or non-coding sequence, an exon with or without an intron from a genomic DNA molecule.

The phrase "cDNA encoding a protein" refers to a nucleic acid sequence that closely aligns with sequences which encode conserved regions, motifs or domains that were identified by employing analyses well known in the art. These analyses include BLAST (Basic Local Alignment Search Tool; Altschul (1993) J Mol Evol 36: 290–300; Altschul et al (1990) J Mol Biol 215:403–410) which provides identity within the conserved region. Brenner et al. (1998; Proc Natl Acad Sci 95:6073–6078) who analyzed BLAST for its ability to identify structural homologs by sequence identity found 30% identity is a reliable threshold for sequence alignments of at least 150 residues and 40% is a reasonable threshold for alignments of at least 70 residues (Brenner et al. page 6076, column 2).

"Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased, upregulated or present, or decreased, downregulated or absent, gene expression as detected by the absence, presence, or at least two-fold changes in the amount of transcribed messenger RNA or translated protein in a sample.

"Disorder" refers to conditions, diseases or syndromes in which the cDNAs and MAPOP-1 are differentially expressed. These include cell proliferative disorders, particularly cancers, and autoimmune disorders, particularly Crohn's disease.

"Fragment" refers to a chain of consecutive nucleotides from about 200 to about 700 base pairs in length. Fragments may be used in PCR or hybridization technologies to identify related nucleic acid molecules and in binding assays to screen for a ligand. Nucleic acids and their ligands identified in this manner are useful as therapeutics to regulate replication, transcription, or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. The degree of complementarity and the use of nucleotide analogs affect the efficiency and stringency of hybridization reactions.

"Ligand" refers to any agent, molecule, or compound which will bind specifically to a complementary site on a cDNA molecule or polynucleotide or to an epitope or a protein. Such ligands stabilize or modulate the activity of polynucleotides or proteins and may be composed of inorganic or organic substances including nucleic acids, proteins, carbohydrates, fats, and lipids.

"Oligonucleotide" refers a single stranded molecule from about 18 to about 60 nucleotides in length which may be used in hybridization or amplification technologies or in regulation of replication, transcription, or translation. Substantially equivalent terms are amplimer, primer, and oligomer.

"Portion" refers to any part of a protein used for any purpose, but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid in a sample. Where targets are single stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR, Madison Wis.). An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate a cell; a tissue a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al (1997) Nucleic Acids Res 25:3389–3402). BLAST2 may be used in a standardized and reproducible way to insert gaps in one of the sequences in order to optimize alignment and to achieve a more meaningful comparison between them.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA or a protein encoded by the cDNA. Such variants contain characteristic, conserved domains and motifs with high similarity to those of protein families found in PFAM, BLOCKS and PRINTS databases. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid.

THE INVENTION

The invention is based on the discovery of a cDNA which encodes an RVP-1 variant (MAPOP-1) and on the use of the cDNA, or fragments thereof, and protein, or portions thereof, directly or as compositions in the characterization, diagnosis, and treatment of cell proliferative disorders, particularly cancers, and autoimmune disorders, particularly Crohn's disease.

Nucleic acids encoding the RVP-1 variant, MAPOP-1 (FIGS. 1A–1C), of the present invention were first identified in Incyte Clone 1456746 from the fetal colon cDNA library (COLNFET02) using a computer search for amino acid sequence alignments. A consensus sequence, SEQ ID NO:2, was derived from the following overlapping and/or extended nucleic acid sequences (SEQ ID NO:3–7): Incyte clones 1456746H1 (COLNFET02), 1512130H1 (LUNGNOT14), 1456746T6 (COLNFET02), 2922036H1 (SININOT04), and 1430349F1 (SINTBST01). Northern analysis showed the expression of this sequence in various libraries, at least 65% of which are associated with cancer or proliferating cells and at least 29% of which are associated with the immune response or trauma. In particular, 35% of the libraries expressing RVP-1 are derived from gastrointestinal tissue and 29% are derived from reproductive tissue. FIG. 3A shows the differential expression of SEQ ID NO:2 in libraries constructed from tissues removed from patients with Crohn's disease. FIG. 3B shows the libraries constructed from tissues removed from patients with ulcerative colitis in which SEQ ID NO:2 was never expressed. Therefore, the cDNA is useful in assays to distinguish between Crohn's disease and ulcerative colitis. A fragment of the cDNA from about nucleotide 1531 to about nucleotide 1591 is also useful in diagnostic assays.

Figure 2B:
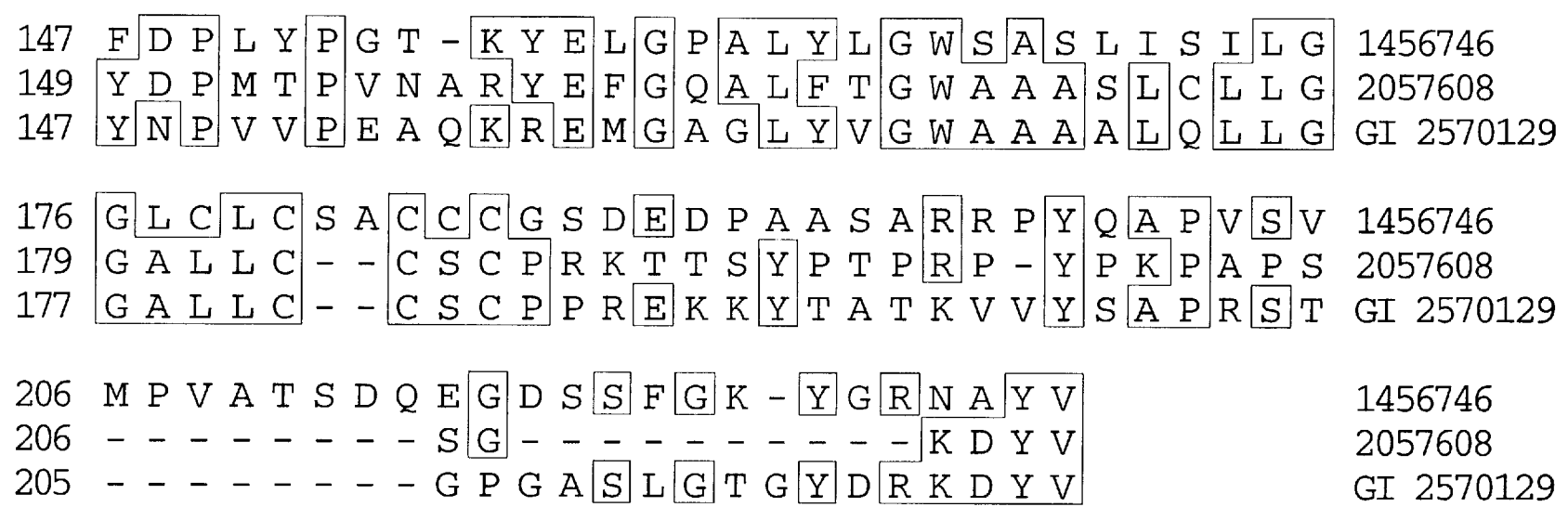

In one embodiment, the invention encompasses a polypeptide comprising the amino acid sequence of SEQ ID NO:1. MAPOP-1 is 228 amino acids in length and has one potential N-glycosylation site at N141; four potential casein kinase II phosphorylation sites at T43, T154, S187, and S211; two potential protein kinase C phosphorylation sites at S111 and S194, and one potential tyrosine kinase phosphorylation site at Y151. A signal peptide sequence is predicted from M1 to P25. BLOCKS analysis indicates that the regions of MAPOP-1 from S2 to V31, from I44 to L57, from M68 to E109, and from L158 to C185 are similar to PMP-22/EMP/MP20 family motifs. Such motifs are characteristic of small integral membrane glycoproteins found in neural, tumor, and epithelial cells. In addition, PRINTS analysis indicates that the regions of MAPOP-1 from T7 to S32, from Y74 to I105, from H124 to I142, and from L162 to C180 are similar to transmembrane domains in the rhesus blood group proteins. As shown in FIGS. 2A and 2B, MAPOP-1 has chemical and structural similarity with clone 2057608 (claudin 1) and hRVP1 (g2570129, SEQ ID NO:13). In particular, MAPOP-1 and hRVP1 share 33% identity. Several residues including P25, W29, W49, C52, C62, S67, R79, F146, and C185 are conserved among these four transmembrane proteins. The cyclic amino acid proline and the aromatic amino acids (F and W) are particularly important relative to folding whereas the sulfhydral bonds of the cysteines are important in binding one adhesion molecule to another. Hydrophobicity plots and Hidden Markov Model analysis demonstrate that the four transmembrane domains of hRVP1 are well conserved in MAPOP-1 and extend from about M1 to L20; A80 to L100; I125 to F140; and P160 to C185. An antigenic epitope extends from about F140 to about P160 of SEQ ID NO:2 and a biologically active portion (binding region) of MAPOP-1 extends from about C185 to about F219 of SEQ ID NO:2. An antibody which specifically binds MAPOP-1 is useful in a diagnostic assay to distinguish between Crohn's disease and ulcerative colitis. Such an antibody is also useful in MRI imaging of the gastrointestinal system during inflammation.

Mammalian variants of the cDNA having the nucleic acid sequence of SEQ ID NO:2 were identified using BLAST2 with default parameters against the ZOOSEQ databases (Incyte Genomics). Mammalian variants of SEQ ID NO:2 include 700276486 (RASINOT01), 700277065 (RASINOT01), and 702156327 (template), SEQ ID NOs:8–11, respectively. These preferred variants have from about 80% to about 90% identity over the length of the nucleotide alignment as shown in the table below. The first column presents SEQ ID number for the mammalian cDNAs the second column, the clone number for the mammalian cDNAs; the third column, the percent identity to the SEQ ID NO:2; and the fourth column, the nucleotide alignment between the mammalian cDNA and SEQ ID NO:2 as the latter is shown in the Sequence Listing.

| SEQ ID | Clone No | Identity | Nt Alignment |
| --- | --- | --- | --- |
| 8 | 700276486 | 88% | 309–443 |
| 9 | 700277065 | 83% | 715–854 |
| 10 | 702156327 | 82% | 490–902 |

These cDNAs are particularly useful for producing transgenic cell lines or organisms which model human cell proliferative disorders, particularly cancers, and autoimmune disorders, particularly Crohn's disease. They are also useful for pretesting the toxicity and/or efficacy of therapeutic molecules including antagonists and antibodies that might be used to treat such disorders.

It will be appreciated by those skilled in the art that as a result of the degeneracy of the genetic code, a multitude of cDNA encoding MAPOP-1, some bearing minimal similarity to the cDNAs of any known and naturally occurring gene, may be produced. Thus, the invention contemplates each and every possible variation of cDNA that could be made by selecting combinations based on possible codon choices. These combinations are made in accordance with the standard triplet genetic code as applied to the polynucleotide encoding naturally occurring HSTK, and all such variations are to be considered as being specifically disclosed.

The cDNA and fragments thereof (SEQ ID NOs:2–11) may be used in hybridization, amplification, and screening technologies to identify and distinguish among SEQ ID NO:2 and related molecules in a sample. The mammalian cDNAs may be used to produce transgenic cell lines or organisms which are model systems for Crohn's disease and upon which the toxicity and efficacy of potential therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

Characterization and Use of the Invention
cDNA Libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. Three library preparations representative of the invention are described in the EXAMPLES below. The consensus sequences were chemically and/or electronically assembled from fragments including Incyte clones and extension and/or shotgun sequences using computer programs such as PHRAP (Phil Green, University of Washington, Seattle, Wash.), and AUTOASSEMBLER application (Applied Biosystems, Foster City, Calif.). Clones, extension and/or shotgun sequences are electronically assembled into clusters and/or master clusters.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech (APB), Piscataway, N.J.), or combinations of polymerases and proofreading exonucleases such as those found in the ELONGASE amplification system (Life Technologies, Gaithersburg, Md.). Preferably, sequence preparation is automated with machines such MICROLAB 2200 system (Hamilton, Reno, Nev.) and the DNA ENGINE thermal cycler (MJ Research, Watertown, Mass.). Machines commonly used for sequencing include the ABI PRISM 3700, 377 or 373 DNA sequencing systems (Applied Biosystems), the MEGABACE 1000 DNA sequencing system (APB), and the like. The sequences may be analyzed using a variety of algorithms well known in the art and described in Ausubel et al (1997; *Short Protocols in Molecular Biology*, John Wiley & Sons, New York, N.Y., unit 7.7) and in Meyers (1995; *Molecular Biology and Biotechnology*, Wiley VCH, New York, N.Y., pp. 856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195–202) which are well known in the art. Contaminating sequences including vector or chimeric sequences or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (Applied Biosystems), nested primers, and commercially available cDNA or genomic DNA libraries may be used to extend the nucleic acid sequence. For all PCR-based methods, primers may be designed using commercially available software, such as OLIGO 4.06 primer analysis software (Molecular Biology Insights, Cascade, Col.) to be about 22 to 30 nucleotides in length, to have a GC content of about 50% or more, and to anneal to a target molecule at temperatures from about 55C to about 68C. When extending a sequence to recover regulatory elements, it is preferable to use genomic, rather than cDNA libraries.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding MAPOP-1, allelic variants, or related molecules. The probe may be DNA or RNA, may be single stranded and should have at least 50% sequence identity to any of the nucleic acid sequences, SEQ ID NOs:2–11. Hybridization probes may be produced using oligolabeling, nick translation, end-labeling, or PCR amplification in the presence of a reporter molecule. A vector containing the cDNA or a fragment thereof may be used to produce an mRNA probe in vitro by addition of an RNA polymerase and labeled nucleotides. These procedures may be conducted using commercially available kits such as those provided by APB.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60C, which permits the formation of a hybridization complex between nucleic acid sequences that contain some mismatches. Subsequent washes are performed at higher stringency with buffers such as 0.2×SSC with 0.1% SDS at either 45C (medium stringency) or 68C (high stringency). At high stringency, hybridization complexes will remain stable only where the nucleic acids are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or TRITON X-100 (Sigma-Aldrich, St. Louis, Mo.) and a blocking agent such as denatured salmon sperm DNA. Selection of components and conditions for hybridization are well known to those skilled in the art and are reviewed in Ausubel (supra) and Sambrook et al (1989) *Molecular Cloning, A Laboratory Manual*, Cold Spring Harbor Press, Plainview, N.Y.

Arrays may be prepared and analyzed using methods known in the art. Oligonucleotides may be used as either probes or targets in an array. The array can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al (1995) U.S. Pat. No. 5,474,796; Schena et al (1996) Proc Natl Acad Sci 93:10614–10619; Baldeschweiler et al (1995) PCT application WO95/251116; Shalon et al (1995) PCT application WO95/35505; Heller et al (1997) Proc Natl Acad Sci 94:2150–2155; and Heller et al (1997) U.S. Pat. No. 5,605,662.)

Hybridization probes are also useful in mapping the naturally occurring genomic sequence. The probes may be hybridized to: 1) a particular chromosome, 2) a specific region of a chromosome, 3) an artificial chromosome construction such as human artificial chromosome (HAC), yeast artificial chromosome (YAC), bacterial artificial chromosome (BAC), bacterial P1 construction, or 4) single chromosome cDNA libraries.

Expression

Any one of a multitude of cDNAs encoding MAPOP-1 may be cloned into a vector and used to express the protein, or portions thereof, in host cells. The nucleic acid sequence can be engineered by such methods as DNA shuffling (U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors, yeast transformed with yeast expression vectors insect cell systems transformed with baculovirus expression vectors, plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla, Calif.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using culture techniques. Visible markers are also used to quantify the amount of protein expressed by the introduced genes. Verification that the host cell contains the desired mammalian cDNA is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas, Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), 6×His, FLAG, MYC, and the like. GST and 6×His are purified using commercially available affinity matrices such as immobilized glutathione and metal-chelate resins, respectively. FLAG and MYC are purified using commercially available monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivatized amino acids, and washing with dichloromethane and/or N, N-dimethylformamide. The peptide is cleaved between the peptide carboxy terminus and the linker group to yield a peptide acid or amide. (Novabiochem 1997/98 Catalog and Peptide Synthesis Handbook, San Diego, Calif. pp. S1–S20). Automated synthesis may also be carried out on machines such as the ABI 431A peptide synthesizer (Applied Biosystems). A protein or portion thereof may be substantially purified by preparative high performance liquid chromatography and its composition confined by amino acid analysis or by sequencing (Creighton (1984) *Proteins Structures and Molecular Properties*, W. H. Freeman, New York, N.Y.).

Preparation and Screening of Antibodies

Various hosts including goats, rabbits, rats, mice, humans, and others may be immunized by injection with MAPOP-1 or any portion thereof Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al (1975) Nature 256:495–497; Kozbor et al (1985) J. Immunol Methods 81:3142; Cote et al (1983) Proc Natl Acad Sci 80:2026–2030; and Cole et al (1984) Mol Cell Biol 62:109–120.)

Alternatively, techniques described for the production of single chain antibodies may be adapted, using methods known in the art, to produce epitope-specific, single chain antibodies. Antibody fragments which contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al (1989) Science 246:1275–1281.)

The MAPOP-1 or a portion thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa, N.J.).

Labeling of Molecules for Assay

A wide variety of reporter molecules and conjugation techniques are known by those skilled in the art and may be used in various nucleic acid, amino acid, and antibody assays. Synthesis of labeled molecules may be achieved using commercially available kits (Promega, Madison, Wis.) for incorporation of a labeled nucleotide such as $^{32}$P-dCTP (APB), Cy3-dCTP or Cy5-dCTP (Operon Technologies, Alameda, Calif.), or amino acid such as $^{35}$S-methionine (APB). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene, Oreg.).

DIAGNOSTICS

The cDNAs, fragments, oligonucleotides, complementary RNA and DNA molecules, and PNAs and may be used diagnostically to differentiate between Crohn's disease and ulcerative colitis. The diagnostic assay may use hybridization or amplification technology to compare gene expression in a biological sample from a patient to standard samples in order to detect differential gene expression. Qualitative or quantitative methods for this comparison are well known in the art.

For example, the cDNA or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a substantially purified sequence is used. Standard values obtained in this manner may be compared with values obtained from samples from patients who were diagnosed with a particular condition, disease, or disorder. Deviation from standard values toward those associated with a particular disorder is used to diagnose that disorder.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Similarly, antibodies which specifically bind MAPOP-1 may be used diagnostically on biopsied tissues to differentiate between Crohn's disease and ulcerative colitis.

In addition, antibodies labeled with gold or magnitite particles may be delivered orally for visualization of gastrointestinal tissues using MRI (Ozawa et al (2000) Recent Results Cancer Res 155:73–87). These antibodies ma! also be used to monitor protein being released into the intestine as cells deteriorate during the acute phase of the disease or to assess the effect of therapeutic intervention as patients approach remission.

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based inmmunoassay utilizing monoclonal antibodies reactive to two non-interfering epitopes is preferred, but a competitive binding assay may be employed. (See, e.g., Coligan et al (1997) Current Protocols in Immunology, Wiley-Interscience, New York, N.Y.; and Pound, supra.)

THERAPEUTICS

Chemical and structural similarity, in the context of the conserved residues and transmembrane domains, exists between MAPOP-1 (SEQ ID NO:1), clone 2057608 (claudin 1), and hRVP1 (g2570129; SEQ ID NO:13) as shown in FIG. 2. As shown in FIG. 3, SEQ ID NO:2 is differentially expressed in gastrointestinal tissues and clearly plays a role in cell proliferative disorders, particularly cancers, and autoimmune disorders, particularly Crohn's disease.

Since cancers and autoimmune diseases, particularly Crohn's disease, are associated with increased expression of MAPOP-1, it is desirable to decrease expression or protein activity. In one embodiment, an inhibitor, antagonist or antibody of the protein may be administered to a subject to treat a disorder associated with the increased expression or activity of the endogenous protein. In another embodiment, a vector expressing the complement of the cDNA or fragments thereof may be administered to a subject to treat the disorder. In an additional embodiment, a composition comprising an inhibitor, antagonist or antibody or a vector expressing the complement of the cDNA in conjunction with a pharmaceutical carrier may be administered to a subject to treat the disorder.

Any of the cDNAs, complementary molecules, or fragments thereof, proteins or portions thereof, vectors delivering these nucleic acid molecules or expressing the proteins, and their ligands (antibody, antagonist or inhibitor) may be administered in combination with other therapeutic agents. Selection of the agents for use in combination therapy may be made by one of ordinary skill in the art according to conventional pharmaceutical principles. A combination of therapeutic agents may act synergistically to affect treatment of a particular disorder at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the gene encoding MAPOP-1. Oligonucleotides designed with reference to the transcription initiation site are preferred. Similarly, inhibition can be achieved using triple helix base-pairing which inhibits the binding of polymerases, transcription factors, or regulatory molecules (Gee et al In: Huber and Carr (1994) Molecular and Inmnunologic Approaches, Futura Publishing, Mt. Kisco, N.Y., pp. 163–177). A complementary molecule may also be designed to block translation by preventing binding between ribosomes and mRNA. In one alternative, a library or plurality of cDNAs or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothloate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening and Purification Assays

The cDNA encoding MAPOP-1 may be used to screen a library of molecules or compounds for specific binding affinity. The libraries may be aptamers, DNA molecules, RNA molecules, PNAs, peptides, proteins such as transcription factors, enhancers, repressors, and other ligands which regulate the activity, replication, transcription, or translation of the cDNA in the biological system. The assay involves combining the cDNA or a fragment thereof with the library of molecules under conditions allowing specific binding, and detecting specific binding to identify at least one molecule which specifically binds the single stranded or, if appropriate, double stranded molecule.

In one embodiment, the cDNA of the invention may be incubated with a plurality of purified molecules or compounds and binding activity determined by methods well known in the art, e.g., a gel-retardation assay (U.S. Pat. No. 6,010,849) or a reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay and may be later confirmed by recovering and raising antibodies against that molecule or compound. When these antibodies are added into the assay, they cause a supershift in the gel-retardation assay.

In another embodiment, the cDNA may be used to purify a molecule or compound using affinity chromatography methods well known in the art. In one embodiment, the cDNA is chemically reacted with cyanogen bromide groups on a polymeric resin or gel Then a sample is passed over and reacts with or binds to the cDNA. The molecule or compound which is bound to the cDNA may be released from the cDNA by increasing the salt concentration of the flow-through medium and collected.

In a further embodiment, the protein or a portion thereof may be used to purify a ligand from a sample. A method for using a mammalian protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

In a preferred embodiment, MAPOP-1 or a portion thereof may be used to screen a plurality of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality or libraries of ligands and the specificity of binding or formation of complexes between the expressed protein and the ligand may be measured. Specific binding between the protein and molecule may be measured. Depending on the kind of library being screened, the assay may be used to identify DNA molecules, RNA molecules, peptide nucleic acids, peptides, proteins, minietics, agonists, antagonists, antibodies, immunoglobulins, inhibitors, and drugs or any other ligand, which specifically binds the protein.

In one aspect, this invention contemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the protein specifically compete with a test compound capable of binding to the protein or oligopeptide or portion thereof Molecules or compounds identified by screening may be used in a mammalian model system to evaluate their toxicity, diagnostic, or therapeutic potential.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions Which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or Linder-express a gene of interest may be inbred and used to model human diseases or to test therapeutic or toxic agents. (See U.S. Pat. No. 5,175,383 and U.S. Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animals ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hiematopoietic lineages, and cardiomyocytes.

Knockout Analysis

In gene knockout analysis, a region of a mammalian gene is enzymatically modified to include a non-mammalian gene such as the neomycin phosphotransferase gene (neo Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae, and the blastulae are implanted as described above. Transgenic progeny or inbred lines are studied and treated with potential pharmaceutical agents to obtain information on treatment of the analogous human condition These methods have been used to model several human diseases.

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and common mamiosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the cDNAs which encode the mammalian protein may be used in any molecular biology techniques that have yet to be developed, provided the new techniques rely on properties of cDNAs that are currently known, including, but not limited to, such properties as the triplet genetic code and specific base pair interactions.

EXAMPLES

I cDNA Library Construction

The COLNFET02 cDNA library was made from RNA isolated from colon tissue of a Caucasian female fetus who died at 20 weeks' gestation. The frozen tissue was homogenized and lysed in guanidinium isothiocyanate solution using a POLYTRON homogenizer (Brinkmarn Instruments, Westbury, N.Y.). The RNA was isolated by centrifugation over a CsCl cushion, extracted with phenol, and precipitated with sodium acetate and ethanol. The RNA preparation was resuspended in RNase-free water, treated with DNase, re-extracted with acid phenol, and reprecipitated with sodium acetate and ethanol.

From each RNA preparation, poly(A+) RNA was isolated using the OLIGOTEX kit (Qiagen, Chatsworth, Calif.). Poly(A+) RNA was used for cDNA synthesis and the cDNA library was constructed according to the recommended protocols in the SUPERSCRIPT plasmid system (Life Technologies). The cDNAs were fractionated on a SEPHAROSE CL4B column (APB), and those cDNAs exceeding 400 bp were ligated into the pINCY plasmid (Incyte Genomics). Recombinant plasmids were transformed into DH5α competent cells (Life Technologies).

II Construction of pINCY Plasmid

The plasmid was constructed by digesting the pSPORT1 plasmid (Life Technologies) with EcoRI restriction enzyme (New England Biolabs, Beverly, Mass.) and filling the overhanging ends using Klenow enzyme (New England Biolabs) and 2'-deoxynucleotide 5'-triphosphates (dNTPs). The plasmid was self-ligated and transformed into the bacterial host, E. coli strain JM 109.

An intermediate plasmid produced by the bacteria (pSPORT 1-ΔRI) showed no digestion with EcoRI and was digested with Hind III (New England Biolabs) and the overhanging ends were again filled in with Klenow and dNTPs. A linker sequence was phosphorylated, ligated onto the 5' blunt end, digested with EcoRI, and self-ligated. Following transformation into JM109 host cells, plasmids were isolated and tested for preferential digestibility with EcoRI, but not with Hind III. A single colony that met this criteria was designated pINCY plasmid.

After testing the plasmid for its ability to incorporate cDNAs from a library prepared using NotI and EcoRI restriction enzymes, several clones were sequenced, and a single clone containing an insert of approximately 0.8 kb was selected from which to prepare a large quantity of the plasmid. After digestion with NotI and EcoRI, the plasmid was isolated on an agarose gel and purified using a QIAQUICK column (Qiagen) for use in library construction.

III Isolation and Sequencing of cDNA Clones

Plasmid DNA was released from the cells and purified using the REAL PREP 96 plasmid kit (Qiagen). The recommended protocol was employed except for the following changes 1) the bacteria were cultured in 1 ml of sterile TERRIFIC BROTH (BD Biosciences, Sparks, Md.) with carbenicillin at 25 mg/L and glycerol at 0.4%; 2) after the cultures were incubated for 19 hours, the cells were lysed with 0.3 ml of lysis buffer; and 3) following isopropanol precipitation, the plasmid DNA pellets were each resuspended in 0.1 ml of distilled water. The DNA samples were stored at 4° C.

The cDNAs were prepared for sequencing using either an ABI CATALYST 800 (Applied Biosystems) or a MICROLAB 2200 system (Hamilton) in combination with DNA ENGINE thermal cyclers (MJ Research). The cDNAs were sequenced by the method of Sanger and Coulson (1975; J Mol Biol 94:441–448) using ABI PRISM 373 or 377 sequencing systems (Applied Biosystems) or the MEGABACE 1000 DNA sequencing system (APB). Most of the isolates were sequenced according to standard ABI protocols and kits (Applied Biosystems) with solution volumes of 0.25x–1.0x concentrations. In the alternative, cDNAs were sequenced using solutions and dyes from APB. Reading frames were determined using standard methods. Some of the cDNA sequences were selected for extension using the techniques disclosed below.

IV Extension of cDNA Sequences

The cDNAs were extended using the cDNA clone and oligonucleotide primers. One primer was synthesized to initiate 5' extension of the known fragment, and the other, to initiate 3' extension of the known fragment. The initial primers were designed using OLIGO 4.06 software (Molecular Biology Insights), to be about 22 to 30 nucleotides in length, to have a GC content of about 50% or more, and to anneal to the target sequence at temperatures of about 68C to about 72C. Any stretch of nucleotides that would result in hairpin structures and primer-primer dimerizations was avoided.

Selected cDNA libraries were used as templates to extend the sequence. If more than one extension was necessary, additional or nested sets of primers were designed. Preferred libraries have been size-selected to include larger cDNAs and random primed to contain more sequences with 5' or upstream regions of genes. Genomic libraries are used to obtain regulatory elements, especially extension into the 5' promoter binding region.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94C, three min; Step 2: 94C, 15 sec; Step 3: 60C, one min Step 4: 68C, two min; Step 5: Steps 2, 3, and 4 repeated 20 times; Step 6: 68C, five min; and Step 7: storage at 4C. In the alternative, the parameters for primer pair T7 and SK+(Stratagene) were as follows: Step 1: 94C, three min; Step 2: 94C, 15 sec; Step 3: 57C, one min; Step 4: 68C, two min; Step 5: Steps 2, 3, and 4 repeated 20 times; Step 6: 68C, five min; and Step 7: storage at 4C.

The concentration of DNA in each well was determined by dispensing 100 μl PICOGREEN quantitation reagent (0.25% reagent in 1x TE, v/v, Molecular Probes) and 0.5 μl of undiluted PCR product into each well of an opaque fluorimeter plate (Coming, Acton, Mass.) and allowing the DNA to bind to the reagent. The plate was scanned in a Fluoroskani II (Labsystems Oy) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended clones were desalted, concentrated, transferred to 384-well plates, digested with CviJI cholera virus endonuclease (Molecular Biology Research, Madison, Wis.), and sonicated or sheared prior to religation into pUC18 vector (APB) For shotgun sequences, the digested nucleotide sequences were separated on low concentration (0.6 to 0.8%) agarose gels, fragments were excised, and the agar was digested with AGARACE enzyme (Promega) Extended clones were religated using T4 DNA ligase (New England Biolabs) into pUC18 vector (APB), treated with Pfu DNA polymerase (Stratagene) to fill-in restriction site overhangs, and transfected into E. coli competent cells. Transformed cells were selected on antibiotic-containing media, and individual colonies were picked and cultured overnight at 37C in 384-well plates in LB/2x carbenicillin liquid media.

The cells were lysed, and DNA was amplified using primers, Taq DNA polymerase (APB) and Pfu DNA polymerase (Stratagene) with the following parameters: Step 1: 94C, three min; Step 2: 94C, 15 sec; Step 3: 60C, one min; Step 4: 72C, two min; Step 5: steps 2, 3, and 4 repeated 29 times; Step 6: 72C, five min; and Step 7: storage at 4C. DNA was quantified using PICOGREEN quantitative reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the ABI PRISM BIGDYE terminator cycle sequencing kit (Applied Biosystems).

V. Homology Searching of cDNA Clones and Their Deduced Proteins

The polynucleotide sequences derived from cDNA, extension, and shotgun sequencing were assembled and analyzed using a combination of software programs which utilize algorithms well known to those skilled in the art. Table 1 summarizes the software programs, their descriptions, references, and threshold parameters where applicable.

The polynucleotide sequences were validated by removing vector, linker, and polyA tail sequences and by masking ambiguous bases using algorithms and programs based on BLAST, dynamic programming, and dinucleotide nearest neighbor analysis. All of the sequences disclosed in this application have lengths of at least 49 nucleotides, and no more than 12% uncalled bases (where N is recorded rather than A, C, G, or T). The sequences were queried against a selection of public databases such as GenBank and BLOCKS to acquire annotation, using programs based on BLAST, FASTA, and BLIMPS. The sequences were assembled using Phred, Phrap, and Consed and were analyzed for open reading frames using programs based on GeneMark, BLAST, and FASTA. This was followed by translation of the full length polynucleotide sequences to derive the corresponding full length amino acid sequences. These full length polynucleotide and amino acid sequences were subsequently analyzed by querying against GenBank (primate, rodent, mammalian, vertebrate, eukaryote, and prokaryote), SwissProt, BLOCKS, PRINTS, PFAM, and Prosite databases.

BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the electronic stringency for an exact match was set at 70, and the conservative lower limit for an exact match was set at approximately 40 (with 1–2% error due to uncalled bases).

The BLAST software suite, freely available sequence comparison algorithms (NCBI, Bethesda, Md.; http://www.ncbi.nlm.nih.gov/gorf/bl2.html), includes various sequence analysis programs including "blastn" that is used to align nucleic acid molecules and BLAST 2 that is used for direct pairwise comparison of either nucleic or amino acid molecules. BLAST programs are commonly used with gap and other parameters set to default settings, e.g.: Matrix: BLOSUM62; Reward for match: 1; Penalty for mismatch: −2; Open Gap: 5 and Extension Gap: 2 penalties; Gap×drop-off: 50; Expect: 10; Word Size: 11; and Filter: on. Identity or similarity is measured over the entire length of a sequence or some smaller portion thereof. Brenner et al. (supra, incorporated herein by reference) analyzed the BLAST for its ability to identity structural homologs by sequence identity and found 30% identity is a reliable threshold for sequence alignments of at least 150 residues and 40%, for alignments of at least 70 residues.

The mammalian cDNAs of this application were compared with assembled consensus sequences or templates found in the LIFESEQ GOLD database. Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another and those having local similarity of at least 82% were combined and reassembled. Bins having templates with less than 95% local identity were split. Templates were subjected to analysis by STITCHER/EXON MAPPER algorithms that analyze the probabilities of the presence of splice variants, alternatively spliced exons, splice Junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1\times10^{-8}$. The templates were also subjected to frameshift FASTx against GENPEPT, and homolog match was defined as having an E-value of $\leq 1\times10^{-8}$. Template analysis and assembly was described in U.S. Ser. No. 09/276,534 filed Mar. 25, 1999.

Following assembly, templates were subjected to BLAST, motif, and other functional analyses and categorized in protein hierarchies using methods described in U.S. Ser. No. 08/812,290 and U.S. Ser. No. 08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis, Mo.; http://pfam.wustl.edu/).

VI Chromosome Mapping

Radiation hybrid and genetic mapping data available from public resources such as the Stanford Human Genome Center (SHGC), Whitehead Institute for Genome Research (WIGR), and Genethon are used to determine if any of the cDNAs presented in the Sequence Listing have been mapped. Any of the fragments of the cDNA encoding MAPOP-1 that have been mapped result in the assignment of all related regulatory and coding sequences mapping to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VII Hybridization Technologies and Analyses

Immobilization of cDNAs on a Substrate

The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37C for 16 hr. The membrane is removed from the agar and consecutively placed colony side up in 10% SDS, denaturing solution (1.5 M NaCl, 0.5 M NaOH), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 µg. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807, 522. Polymer-coated slides are prepared by cleaning glass microscope slides (Corning, Acton, Mass.) by ultrasound in 0.1% SDS and acetone, etching in 4% hydrofluoric acid (VWR Scientific Products, West Chester, Pa.), coating with 0.05% aminopropyl silane (Sigma Aldrich) in 95% ethanol, and curing in a 110C oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford, Mass.) for 30 min at 60C; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 µl TE buffer, denaturing by heating to 100C for five min, and briefly centrifuging. The denatured cDNA is then added to a REDIPRIME tube (APB), gently mixed until blue color is evenly distributed, and briefly centrifuged. Five µl of [$^{32}$P]dCTP is added to the tube, and the contents are incubated at 37C for 10 min. The labeling reaction is stopped by adding 5 µl of 0.2M EDTA, and probe is purified from unincorporated nucleotides using a PROBEQUANT G-50 microcolumn (APB). The purified probe is heated to 100C for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMBRIGHT kit (Incyte Genomics) by diluting mRNA to a concentration of 200 ng in 9 µl TE buffer and adding 5 µl 5× buffer, 1 µl 0.1 M DTT, 3 µl Cy3 or Cy5 labeling mix, 1 µl RNase inhibitor, 1 µl reverse transcriptase, and 5 µl 1× yeast control mRNAs. Yeast control mRNAs are synthesized by in vitro transcription from noncoding yeast genomic DNA (WV. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37C for two hr. The reaction mixture is then incubated for 20 min at 85C, and probes are purified using two successive CHROMA SPIN+TE 30 columns (Clontech, Palo Alto, Calif.). Purified probe is ethanol precipitated by diluting probe to 90 µl in DEPC-treated water, adding 2 µl 1 mg/ml glycogen, 60 µl 5 M sodium acetate, and 300 µl 100% ethanol The probe is centrifuged for 20 min at 20,800×g, and the pellet is resuspended in 12 µl resuspension buffer, heated to 65C for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1× high phosphate buffer (0.5 M NaCl, 0.1 M $Na_2HPO_4$, 5 mM EDTA, pH 7) at 55C for two hr. The probe, diluted in 15 ml fresh hybridization solution, is then added to the membrane. The membrane is hybridized with the probe at 55C for 16 hr. Following hybridization, the membrane is washed for 15 min at 25C in 1 mM Tris (pH 8.0), 1% Sarkosyl, and four times for 15 min each at 25C in 1 mM Tris (pH 8.0). To detect hybridization complexes, XOMAT-AR film (Eastman Kodak, Rochester, N.Y.) is exposed to the membrane overnight at −70C, developed, and examined visually.

Polymer Coated Slide-based Hybridization

Probe is heated to 65C for five min, centrifuged five min at 9400 rpm in a 5415C microcentriftige (Eppendorf Scientific, Westbury, N.Y.), and then 18 µl is aliquoted onto the array surface and covered with a coverslip. The arrays are transferred to a waterproof chamber having a cavity just slightly larger than a microscope slide. The chamber is kept at 100% humidity internally by the addition of 140 µl of 5×SSC in a corner of the chamber The chamber containing the arrays is incubated for about 6.5 hr at 60C. The arrays are Washed for 10 min at 45C in 1×SSC, 0.1% SDS, and three times for 10 min each at 45C in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to substantially equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara, Calif.) capable of generating spectral lines at 488 nm for excitation of Cy3 and at 632 nm for excitation of Cy5. The excitation laser light is focused on the array using a 20× microscope objective (Nikon, Melville, N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater, N.J.) corresponding to the two fluorophores. Appropriate filters positioned between the array and the photomultiplier tubes are used to filter the signals. The emission maxima of the fluorophores used are 565 nm for Cy3 and 650 nm for Cy5. The sensitivity of the scans is calibrated using the signal intensity generated by the ,east control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood, Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

VIII Northern Analysis

BLAST was used to search for identical or related molecules in the GenBank or LIFESEQ databases (Incyte Genomics). The product score for human and rat sequences was calculated as follows: the BLAST score is multiplied by the % nucleotide identity and the product is divided by (5 times the length of the shorter of the two sequences), such that a 100% alignment over the length of the shorter sequence gives a product score of 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

All sequences and cDNA libraries in the LIFESEQ database (Incyte Genomics) were categorized by system, organ/ tissue and cell type. The categories included cardiovascular system, connective tissue, digestive system, embryonic structures, endocrine system, exocrine glands, female and male genitalia, germ cells, hemic/immune system, liver, musculoskeletal system, nervous system, pancreas, respiratory system, sense organs, skin, stomatognathic system, unclassified/mixed, and the urinary tract. For each category, the number of libraries in which the sequence was expressed were counted and shown over the total number of libraries in that category. In a non-normalized library, expression levels of two or more are significant.

Electronic northern analysis as described in U.S. Pat. No. 5,840,484 was used at a product score of 70 to compare SEQ ID NO:2 against all 4,442,057 nucleotide sequences from 1042 cDNA libraries in the LIFESEQ database (Incyte Genomics). SEQ ID NO:2 was expressed in 22 libraries which include 13 cancerous, four imtnune, two fetal and three other (small intestine, kidney and testes) libraries of ontogenetic epidermal derivation. SEQ ID NO:2 is most prevalent in libraries derived from gastrointestinal tissues including colon and small intestine. From a total of 72 colon and small intestine libraries, FIG. 3A and 3B shows the differential expression of SEQ ID NO:2 in Crohn's disease and the absence of expression in libraries from tissues of patients diagnosed with (chronic) ulcerative colitis.

IX Complementary Molecules

Molecules complementary to the cDNA, from about 5 (PNA) to about 5000 bp (complement of a cDNA insert), arc used to detect or inhibit gene expression. These molecules are selected using OLIGO 4.06 software (National Biosciences). Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the mammalian protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if appropriate elements for inducing vector replication are used in the transformation/expression system.

Stable transformation of appropriate dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the mammalian protein.

X Expression of MAPOP-1

Expression and purification of the mammalian protein are achieved using either a mammalian cell expression system or an insect cell expression system. The pUB6/V5-His vector system (Invitrogen, Carlsbad, Calif.) is used to express MAPOP-1 in CHO cells. The vector contains the selectable bsd gene, multiple cloning sites, the promoter/ enhancer sequence from the human ubiquitin C gene, a C-terminal V5 epitope for antibody detection with anti-V5 antibodies, and a C-terminal polyhistidine (6×His) sequence for rapid purification on PROBOND resin (Invitrogen). Transformed cells are selected on media containing blasticidin.

Spodoptera frugiverda (Sf9) insect cells are infected with recombinant Autographica californica nuclear polyhedrosis virus (baculovirus). The polyhedrin gene is replaced with the mammalian cDNA by homologous recombination and the polyhedrin promoter drives cDNA transcription. The protein is synthesized as a fusion protein with 6×his which enables purification as described above. Purified protein is used in the following activity and to make antibodies

XII Production of Antibodies

MAPOP-1 is purified using polyacrylaiide gel electrophoresis and used to immunize mice or rabbits. Antibodies are produced using the protocols below. Alternatively, the amino acid sequence of MAPOP-1 is analyzed using LASERGENE software (DNASTAR) to determine regions of high antigenicity. An antigenic epitope, usually found near the C-terminus or in a hydrophilic region is selected, synthesized, and used to raise antibodies. Typically, epitopes of about 15 residues in length are produced using an ABI 431A peptide synthesizer (Applied Biosystems) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in Incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XII Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein After coupling, the protein is eluted from the column using a buffer of pH 2–3 or a high concentration of urea or thiocyanate ion to disrupt antibody/protein binding, and the protein is collected.

XIV Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FITC (Molecular Probes), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XV Two-Hybrid Screen

A yeast two-hybrid system, MATCHMAKER LexA Two-Hybrid system (Clontech), is used to screen for peptides that bind the mammalian protein of the invention. A cDNA encoding the protein is inserted into the multiple cloning site of a pLecA vector, ligated, and transformed into E. coli. cDNA, prepared from mRNA, is inserted into the multiple cloning site of a pB42AD vector, ligated, and transformed into E. coli to construct a cDNA library. The pLexA plasmid and pB42AD-cDNA library constructs are isolated from E. coli and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30C until the colonies have grown up and are counted. The colonies are pooled in a minimal volume of 1× TE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30C. A sample of the culture is plated on SD/-Trp/-Ura media and incubated at 30C until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, xyhichi contains a cDNA encoding a protein that physically interacts with the mammalian protein, is isolated from the yeast cells and characterized.

XVI MAPOP-1 Assay

MAPOP-1 activity is assayed in BHK cells as described by Stanger (1995; Cell 81:513–523). The cells are seeded on a microscope slide and transiently transformed with the pfNCY vector (Incyte Genomics) containing the cDNA of SEQ ID NO:2 and a plasmid which contains a vector with elements to express B-galactosidase. The cells are fixed after twelve hours and incubated in a buffer containing X-gal to visualize B-galactosidase activity. Phase or interference contrast microscopy is used to examine the transformed cells. Cells expressing both plasmids display intense blue staining due to expression of B-galactosidase and altered membrane structure due to the expression of MAPOP-1.

All patent applications, patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

What is claimed is:

1. An isolated cDNA encoding a protein having the amino acid sequence of SEQ ID NO:1.

2. A composition comprising the cDNA or the complete complement of the cDNA of claim 1.

3. A substrate upon which the composition of claim 2 is immobilized.

4. A probe consisting of the composition of claim 2.

5. A vector comprising the cDNA of claim 1.

6. A host cell comprising the vector of claim 5.

7. A method for producing a protein having the amino acid sequence of SEQ ID NO:1, the method comprising:

a) culturing the host cell of claim 6 under conditions for protein production; and b) recovering the protein so produced from the host cell culture.

8. A nucleic acid molecule which is completely complementary over its full length to the cDNA of claim 1.

9. An isolated cDNA consisting of the nucleic acid sequence of SEQ ID NO:2 or the complete complement of the nucleic acid sequence of SEQ ID NO:2.

* * * * *